United States Patent
Brandish et al.

(10) Patent No.: US 8,063,090 B2
(45) Date of Patent: Nov. 22, 2011

(54) MINERALOCORTICOID RECEPTOR MODULATORS

(75) Inventors: Philip E. Brandish, North Wales, PA (US); James C. Hershey, Collegeville, PA (US); Mark E. Fraley, North Wales, PA (US); Justin T. Steen, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 104 days.

(21) Appl. No.: 12/532,031

(22) PCT Filed: Mar. 19, 2008

(86) PCT No.: PCT/US2008/003600
§ 371 (c)(1),
(2), (4) Date: Sep. 18, 2009

(87) PCT Pub. No.: WO2008/118319
PCT Pub. Date: Oct. 2, 2008

(65) Prior Publication Data
US 2010/0069452 A1    Mar. 18, 2010

Related U.S. Application Data

(60) Provisional application No. 60/919,740, filed on Mar. 23, 2007.

(51) Int. Cl.
*A61K 31/415* (2006.01)
*C07D 233/64* (2006.01)
(52) U.S. Cl. .............. 514/397; 548/311.1; 514/396
(58) Field of Classification Search .............. 548/311.1; 514/397
See application file for complete search history.

(56) References Cited

U.S. PATENT DOCUMENTS 6,451,833 B1 * 9/2002 Bovy et al. ............... 514/397

OTHER PUBLICATIONS

International Search Report for International Application No. PCT/US08/03600, mailed on Jun. 20, 2008 from Authorized Officer Lee W. Young.

* cited by examiner

*Primary Examiner* — Joseph K. McKane
*Assistant Examiner* — Janet L Coppins
(74) *Attorney, Agent, or Firm* — Dianne Pecoraro; Heidi M. Struse; Catherine D. Fitch

(57) ABSTRACT

The present invention relates to diphenylmethyl imidazole mineralocorticoid receptor modulators compounds having the structure

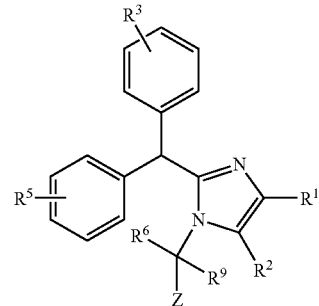

and their use in treating cardiovascular events.

11 Claims, No Drawings

MINERALOCORTICOID RECEPTOR MODULATORS

PRIORITY CLAIM

This application is a §371 National Stage Application of PCT/US2008/003600, filed on Mar. 19, 2008, which claims priority from U.S. Provisional Application Ser. No. 60/919,740, filed on Mar. 23, 2007.

FIELD OF THE INVENTION

The invention relates to novel mineralocorticoid receptor modulators of the general formula (I). The invention also concerns related aspects including processes for the preparation of the compounds, pharmaceutical compositions containing one or more compounds of formula (I) and especially their use as mineralocorticoid receptor modulators in cardiovascular events.

BACKGROUND OF THE INVENTION

The compounds described in this invention represent a novel structural class of mineralocorticoid receptor modulators.

Mineralocorticoids exert profound influences on a multitude of physiological functions by virtue of their diverse roles in growth, development and maintenance of homeostasis. The actions are mediated by the mineralocorticoid receptor. In visceral tissues, such as the kidney and the gut, mineralocorticoid receptors regulate sodium retention, potassium excretion, and water balance in response to aldosterone. Elevations in aldosterone levels, or excess stimulation of mineralocorticoid receptors, are linked to several physiological disorders or pathologic disease states including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels (Hadley, M. E., ENDOCRINOLOGY, $2^{nd}$ Ed., pp. 366-381, (1988); and Brilla et al., Journal of Molecular and Cellular Cardiology, 25(5), pp. 563-575 (1993)). Additionally, elevated aldosterone levels have been increasingly implicated with congestive heart failure (CHF). In CHF, the failing heart triggers hormonal mechanisms in other organs in response to the attending reductions in blood flow and blood pressure seen with CHF. In particular, the kidney activates the rennin-angiotensin-aldosterone system (RAAS) causing an increase in aldosterone production by the adrenals which, in turn, promotes water and sodium retention, potassium loss, and further edema. Although historically it was believed that aldosterone participated in the etiology of CHF only as a result of its salt retaining effects, several recent studies have implicated elevated aldosterone levels with events in extra-adrenal tissues and organs, such as myocardial and vascular fibrosis, direct vascular damage, and baroreceptor dysfunction. Pitt et al., New Eng. J. Med., 341:709-717 (1999). These findings are particularly significant since angiotensin converting enzyme (SCE) inhibitors, which were once thought to completely abolish aldosterone production, are now believed to only transiently suppress aldosterone production which has been shown to occur in extra-adrenal tissues including the heart and vasculature. Weber, New Eng. J. Med., 341:753-755 (1999); Fardella and Miller, Annu Rev. Nutr., 16:443-470 (1996).

The involvement of aldosterone acting via MR in CHF was confirmed in the recently completed RALES (Randomized Aldactone Evaluation Study) study, Pitt et al., New Eng. J. Med., 341:709-717 (1999). The RALES study demonstrated that the use of Aldactone™ (spironolactone), a well-known competitive MR antagonist, in combination with standard CHF therapy, reduced cardiac related mortality by 30% and frequency of hospitalization by 33% in patients suffering from advanced CHF. However, spironolactone therapy has also been associated with attending side effects such as gastric bleeding, diarrhea, azotemia, hyperchloremic metabolic acidosis and type-4 renal tubule acidosis, nausea, gynecomastia, erectile dysfunction, hyperkalemia, and irregular menses. Thus, the mineralocorticoid receptor represents a viable target for CHF therapy either alone or in combination with conventional CHF therapies such as vasodilators (ACE inhibitors), inotropics (digoxin), diuretics, or beta blockers. Molecules, preferably non-steroids, which bind to the mineralocorticoid receptor and modulate receptor activity without the attending side effects current therapies would be particularly desirable.

Current mineralocorticoid receptor antagonists are limited by hyperkalemia due to blockade of renal epithelial mineralocorticoid receptors. Mineralocorticoid receptor antagonists are approved for treatment of hypertension and heart failure. Non-kalemic mineralocorticoid receptor modulators would be safer that current approved compounds.

SUMMARY OF THE INVENTION

The present invention is directed to certain compounds and their use as mineralocorticoid receptor modulators, including treatment of conditions known to be associated with the mineralocorticoid receptor. The invention includes compounds of Formula I

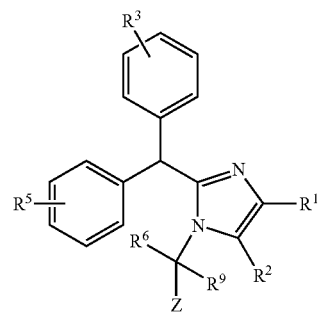

and pharmaceutically acceptable salts thereof, or an optical isomer thereof, wherein
Z is selected from the group consisting of
1) an aryl ring,
2) a heteroaryl ring, wherein the point of attachment to the heteroaryl ring is a carbon atom, and the heteroaryl ring is selected from the group consisting of:
  a) a 5-membered unsaturated monocyclic ring with 1, 2, 3, or 4 heteroatom ring atoms selected from the group consisting of N, O or S,
  b) a 6-membered unsaturated monocyclic ring with 1, 2, 3, or 4 heteroatom ring atoms selected from the group consisting of N, O or S, and
  c) an 8-, 9- or 10-membered unsaturated bicyclic ring with 1, 2, 3, or 4 heteroatom ring atoms selected from the group consisting of N, O or S, and 3) a 4-6 membered saturated heterocyclic ring with 1, 2 or 3 heteroatom ring atoms selected from the group consisting of N, O and S, wherein the point of attachment to the heterocyclic ring is a carbon atom, said aryl, heteroaryl, saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms;

$R^1$ and $R^2$ are selected from the group consisting of hydrogen and $C_1$-$C_6$ alkyl, or $R^1$ and $R^2$, together with the carbon atoms to which they are attached, form a benzimidazole ring substituted at the 1- and 2-positions;

$R^3$ and $R^5$ are selected from the group consisting of hydrogen, halogen, $C_1$-$C_6$ alkyl, $C_1$-$C_6$ alkoxy, OH, and CN;

$R^4$ is selected from the group consisting of $C_1$-$C_6$ alkyl, $C_1$-$C_6$ alkoxy, halogen, $NO_2$, $NH_2$, $CF_3$, $SCF_3$, $NHC(O)R^7$, OH, CN, $NR^aR^b$, $CONR^aR^b$, $CO2Ra$, $C(O)0$-$2R^a$, $SO2NR^aR^b$, where $R^a$ and $R^b$ are independently selected from the group consisting of hydrogen and $C_1$-$C_6$ alkyl, or $R^a$ and $R^b$, together with the N atom to which they are attached, form a 3-8-membered ring containing the N atom and 1-3 heteroatoms selected from the group consisting of N, O and S;

$R^6$ and $R^9$ are independently selected from the group consisting of hydrogen and $C_1$-$C_6$ alkyl;

$R^7$ is selected from the group consisting of
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S, and
   c) an 8-, 9- or 10-membered unsaturated bicyclic ring with 1, 2, 3, or 4 heteroatom ring atoms selected from the group consisting of N, O or S, and
3) $C_1$-$C_6$ alkyl, wherein said aryl ring, heteroaryl ring, and $C_1$-$C_6$ alkyl is unsubstituted, mono-substituted with $R^8$, disubstituted with groups independently selected from $R^8$, trisubstituted with groups independently selected from $R^8$, or tetrasubstituted with groups independently selected from $R^8$, and wherein any stable S or N heteroaryl ring atom is unsubstituted or substituted with oxo, said heteroaryl ring $R^8$, substitutions being on one or more heteroaryl ring carbon atoms; and $R^8$ is independently selected from the group consisting of $C_1$-$C_6$ alkyl, $C_1$-$C_6$ alkoxy, OH, CN and halogen.

DETAILED DESCRIPTION OF THE DISCLOSURE

The compounds of Formula I above, and pharmaceutically acceptable salts thereof, are mineralocorticoid receptor modulators. The compounds are useful for modulating the mineralocorticoid receptor and treating conditions such as hypertension.

In one embodiment, Z is selected from the group consisting of an aryl ring and 9-membered unsaturated heteroaryl bicyclic ring with 1 or 2 heteroatom ring atoms, wherein the heteroatom is O, wherein said aryl or heteroaryl bicyclic ring is unsubstituted, mono-substituted with $R^4$, disubstituted with groups independently selected from $R^4$, trisubstituted with groups independently selected from $R^4$, or tetrasubstituted with groups independently selected from $R^4$, said heteroaryl ring $R^4$ substitutions being on one or more heteroaryl ring carbon atoms, and all other variables are as previously defined. In a preferred group of this embodiment, $R^4$ is selected from the group consisting of $CH_3$, $OCH_3$, halogen, $NO_2$, $NH_2$, $CF_3$, $SCF_3$, Cl, Br, I, and $NHC(O)R^7$, and all other variables are as previously defined. In a more preferred group of this embodiment, $R^7$, is aryl either unsubstituted, mono-substituted with $CH_3$ or Cl, or independently di-substituted with a substituent selected from the group consisting of $CH_3$ and Cl, and all other variables are as previously defined. In an even more preferred group of this embodiment, Z is selected from the group consisting of

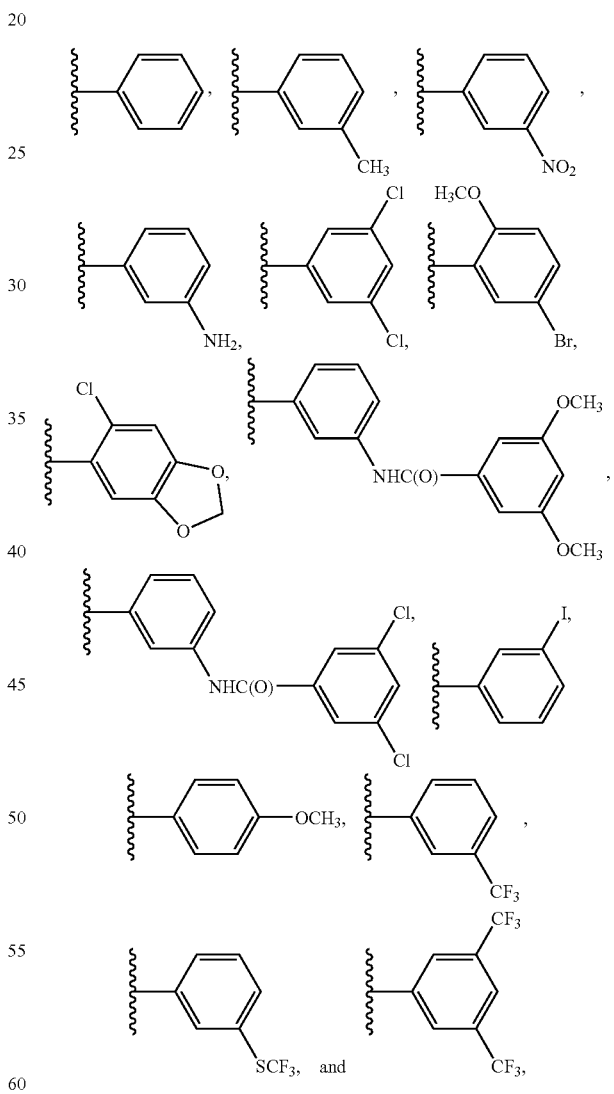

and all other variables are as previously defined.

In another embodiment, $R^1$ and $R^2$ are selected from the group consisting of hydrogen and $CH_3$, or $R^1$ and $R^2$, together with the carbon atoms to which they are attached, form a benzimidazole ring substituted at the 1- and 2-positions.

In another embodiment, $R^3$ and $R^5$ are hydrogen.

In another embodiment, $R^6$ is selected from the group consisting of hydrogen and $CH_3$.

Specific examples of compounds of formula I, and pharmaceutically acceptable salts thereof, include
2-(diphenylmethyl)-1-(1-phenylethyl)-1H-imidazole,
2-(diphenylmethyl)-1-[1-(3-iodophenyl)ethyl]-1H-imidazole,
2-(diphenylmethyl)-1-(4-methoxybenzyl)-1H-imidazole,
2-(diphenylmethyl)-1-[3-(trifluoromethyl)benzyl]-1H-imidazole,
2-(diphenylmethyl)-1-{3-[(trifluoromethyl)thio]benzyl}-1H-imidazole,
1-{1-[3,5-bis(trifluoromethyl)phenyl]ethyl}-2-(diphenylmethyl)-1H-imidazole,
1-[3,5-bis(trifluoromethyl)benzyl]-2-(diphenylmethyl)-1H-imidazole,
2-(diphenylmethyl)-1-(3-iodobenzyl)-1H-imidazole,
2-(diphenylmethyl)-1-(3-methylbenzyl)-1H-imidazole,
2-(diphenylmethyl)-1-(3-nitrobenzyl)-1H-imidazole,
3-{[2-(diphenylmethyl)-1H-imidazol-1-yl]methyl}aniline,
1-[1-(3,5-dichlorophenyl)ethyl]-2-(diphenylmethyl)-1H-imidazole,
1-(5-bromo-2-methoxybenzyl)-2-(diphenylmethyl)-1H-imidazole,
1-[(6-chloro-1,3-benzodioxol-5-yl)methyl]-2-(diphenylmethyl)-1H-imidazole,
N-(3-{[2-(diphenylmethyl)-1H-imidazol-1-yl]methyl}phenyl)-3,5-dimethoxybenzamide,
3,5-dichloro-N-(3-{[2-(diphenylmethyl)-1H-imidazol-1-yl]methyl}phenyl)benzamide,
1-benzyl-2-(diphenylmethyl)-4,5-dimethyl-1H-imidazole,
2-(diphenylmethyl)-1H-benzimidazole,
1-benzyl-2-(diphenylmethyl)-1H-benzimidazole, and
2-(diphenylmethyl)-1-(1-phenylethyl)-1H-benzimidazole.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of the optical isomers and mixtures thereof. Unless specifically mentioned otherwise, reference to one isomer applies to any of the possible isomers. Whenever the isomeric composition is unspecified, all possible isomers are included.

Ac acetyl
nBuLi n-butyl lithium
DMF dimethylformamide
EtOH ethanol
LMRS low resolution mass spectrometry
Me methyl
NMR nuclear magnetic resonance
Pd/C palladium-on-carbon catalyst
THF tetrahydrofuran Embodiments of the method of the present invention include those in which the compound of Formula I administered to the subject is as defined in the compound embodiments, classes and sub-classes set forth above.

As used herein except where noted, "alkyl" is intended to include both branched- and straight-chain saturated aliphatic hydrocarbon groups, and is intended to include the cyclic group cycloalkyl, including all isomers, having the specified number of carbon atoms. The term "cycloalkyl" means carbocycles containing no heteroatoms. Examples of cycloalkyl include cyclopropyl, cyclobutyl, cyclopentyl, cyclohexyl. Commonly used abbreviations for alkyl groups are used throughout the specification, e.g. methyl may be represented by conventional abbreviations including "Me" or $CH_3$ or a symbol that is an extended bond without defined terminal group, e.g.

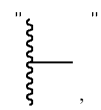

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge. The term "alkanol" in the definition of variable $R^2$ represents a linear or branched alkyl group of indicated number of carbon atoms having at least one hydroxyl substituent, e.g., ethanol., and includes alkanediols and alkanetriols, and attached to the cycloalkyl ring by a carbon-carbon bond.

As used herein except where noted, "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results. Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl). Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 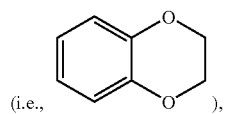 ), imidazo(2,1-b) (1,3)thiazole, (i.e., 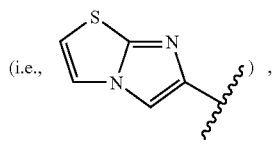 ), and benzo-1,3-dioxolyl (i.e., 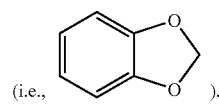 ).

In certain contexts herein,

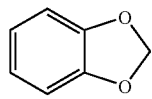

is alternatively referred to as phenyl having as a substituent methylenedioxy attached to two adjacent carbon atoms.

Unless otherwise specifically noted as only "unsubstituted" or only "substituted", defined groups are unsubstituted or substituted. Terms such as "substituted $C_{3-8}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C (O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O) NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "halogen" (or "halo") refers to fluorine, chlorine, bromine and iodine (alternatively referred to as fluoro (F), chloro (Cl), bromo (Br), and iodo (I)).

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

The compounds of Formula I can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Certain of the compounds employed in the present invention may carry an acidic moiety (e.g., —COOH or a phenolic group), in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The invention relates to a method for the treatment and/or prophylaxis of diseases which are related to hypertension, congestive heart failure, pulmonary hypertension, systolic hypertension, renal insufficiency, renal ischemia, renal failure, renal fibrosis, cardiac insufficiency, cardiac hypertrophy, cardiac fibrosis, myocardial ischemia, vascular inflammation, vascular dementia, cardiomyopathy, glomerulonephritis, renal colic, complications resulting from diabetes such as nephropathy, vasculopathy and neuropathy, macular degenerative disorders, metabolic syndrome, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, which method comprises administrating a compound as defined above to a human being or animal.

In another embodiment, the invention relates to a method for the treatment and/or prophylaxis of diseases which are related to hypertension, congestive heart failure, pulmonary hypertension, macular degenerative disorders, metabolic syndrome, intraocular pressure, glaucoma, atherosclerosis, metabolic syndrome, and complications resulting from diabetes such as nephropathy, vasculopathy and neuropathy.

The invention also relates to the use of compounds of formula (I) for the preparation of a medicament for the treatment and/or prophylaxis of the above-mentioned diseases.

Compounds of formula (I) or the abovementioned pharmaceutical compositions are also of use in combination with other pharmacologically active compounds such as antihypertensive or antiinflammatory compounds including ACE-inhibitors, neutral endopeptidase inhibitors, angiotensin II receptor antagonists, renin inhibitors, endothelin receptors antagonists, vasodilators, calcium channel antagonists, potassium activators, diuretics, sympatholitics, beta-adrenergic antagonists, alpha-adrenergic antagonists, other mineralocorticoid receptor modulators, glucorticoids, glucorticoid receptor modulators, estrogen receptor modulators, and androgen receptor modulators and other active compounds commonly administered with antihypertensives to treat diseases associated with hypertension, organ damage and inflammation, including, but not limited to cholesterol reducing statins, cholesterol absorption inhibitors or with other drugs beneficial for the prevention or the treatment of the above-mentioned diseases.

The term "administration" and variants thereof (e.g., "administering" a compound) in reference to a compound of Formula I mean providing the compound or a prodrug of the compound to the individual in need of treatment or prophylaxis. When a compound of the invention or a prodrug thereof is provided in combination with one or more other active agents (e.g., an agent such as an angiotensin II receptor antagonist, renin inhibitor, ACE inhibitor, or other active agent which is known to reduce blood pressure), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit renin and thereby elicit the response being sought (i.e., an "inhibition effective amount"). When the active compound (i.e., active ingredient) is administered as the salt, references to the amount of active ingredient are to the free form (i.e., the non-salt form) of the compound.

In a preferred embodiment, this amount is comprised between 1 mg and 1000 mg per day. In a particularly preferred embodiment, this amount is comprised between 1 mg and 500 mg per day. In a more particularly preferred embodiment, this amount is comprised between 1 mg and 200 mg per day.

In the method of the present invention, the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18th edition, edited by A. R. Gennaro, Mack Publishing Co., 1990.

Compounds of the present invention can be made by a variety of methods depicted in the illustrative synthetic reaction scheme shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2.sup.nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction scheme can be isolated and purified if desired using conventional techniques, including but not limited to, filtration, distillation, crystallization, chromatography, and the like. Such materials can be characterized using conventional means, including physical constants and spectral data.

Unless specifically stated otherwise, the experimental procedures were performed under the following conditions. Evaporation of solvent was carried out using a rotary evaporator under reduced pressure (600-4000 pascals: 4.5-30 mm Hg) with a bath temperature of up to 60° C. Reactions are typically run under nitrogen atmosphere at ambient temperature if not otherwise mentioned. Anhydrous solvent such as THF, DMF, Et$_2$O, DME and Toluene are commercial grade. Reagents are commercial grade and were used without further purification. Flash chromatography is run on silica gel (230-400 mesh). The course of the reaction was followed by either thin layer chromatography (TLC) or nuclear magnetic resonance (NMR) spectrometry and reaction times given are for illustration only. The structure and purity of all final products were ascertained by TLC, mass spectrometry, $^1$H NMR and high-pressure liquid chromatography (HPLC). Chemical symbols have their usual meanings The following abbreviations have also been used: v (volume), w (weight), b.p. (boiling point), m.p. (melting point), L (liter(s)), mL (milliliter(s)), g (gram(s)), mg (milligram(s)), mol (mole(s)), mmol (millimole(s)), eq. (equivalent(s)). Unless otherwise specified, all variables mentioned below have the meanings as provided above.

Compounds of the present invention can be prepared according to the following general methods as exemplified in Scheme 1.

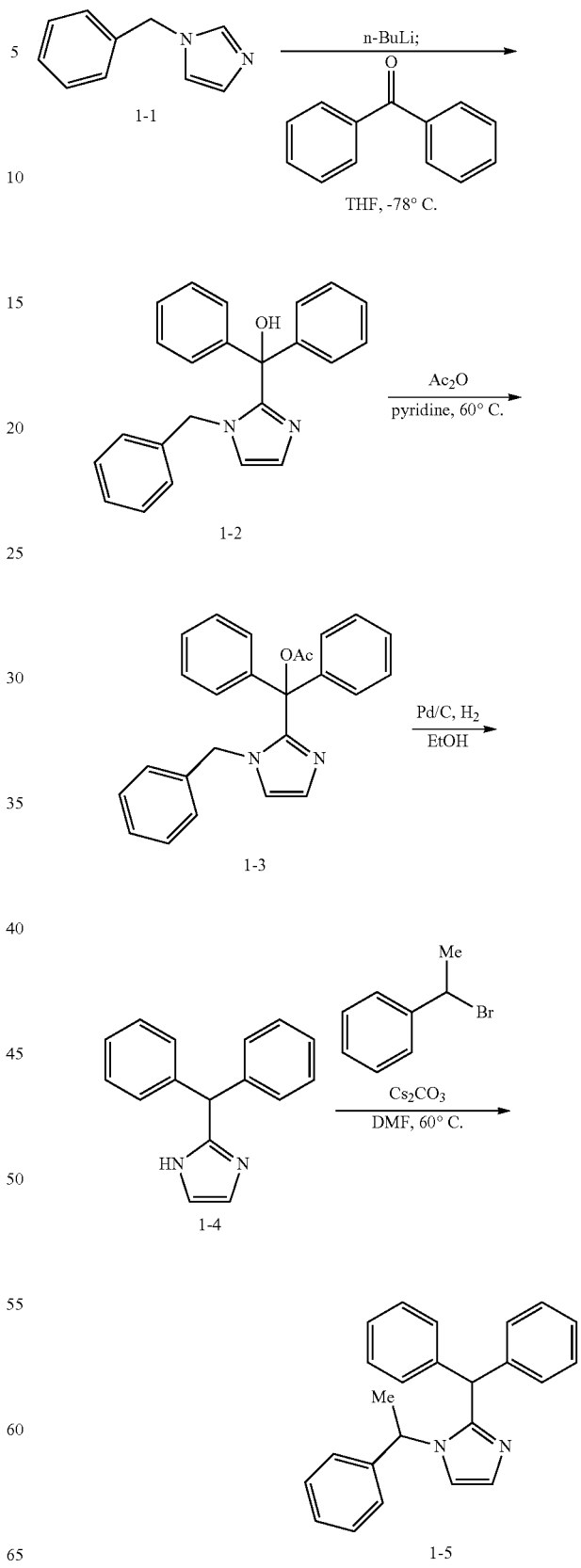

(1-benzyl-1H-imidazol-2-yl)(diphenyl)methanol (1-2)

A solution of n-butyllithium in hexanes (1.6 M, 45.0 mL, 72.0 mmol, 1.14 equiv) was added to a solution of 1-benzylimidazole (1-1, 10.0 g, 63.2 mmol, 1 equiv) in THF (200 mL) at −78° C. and the resulting mixture was stirred for 20 min. A solution of benzophenone (15.5 mL, 95.0 mmol, 1.50 equiv) in THF (30 mL) was added and the reaction mixture was stirred at −78° C. for 1 h, then warmed to 23° C. The mixture was partitioned between saturated ammonium chloride solution (200 mL) and ethyl acetate (400 mL), and the organic layer was separated, dried over magnesium sulfate and concentrated to give a yellow oil. The oil was suspended in saturated aqueous sodium carbonate solution and the resulting precipitate was filtered, washed with water (200 mL) then ethyl ether (2×100 mL) and air dried to afford (1-benzyl-1H-imidazol-2-yl)(diphenyl)methanol (1-2) as a white solid. $^1$H NMR (300 MHz, DMSO) δ 7.25 (m, 12H), 7.04 (m, 2H), 6.93 (s, 2H), 6.78 (s, 1H), 5.02 (s, 2H). LRMS m/z (M−OH) 323.1 found, 323.2 required.

(1-benzyl-1H-imidazol-2-yl)(diphenyl)methyl acetate (1-3)

A slurry of (1-benzyl-1H-imidazol-2-yl)(diphenyl)methanol (1-2, 16.0 g, 47.0 mmol, 1 equiv) in acetic anhydride (120 mL) and pyridine (130 mL) was heated at 60° C. for 18 h. The resulting orange slurry was concentrated to dryness. The residue was suspended in saturated aqueous sodium carbonate solution (300 mL) and the resulting precipitate was filtered and washed with water (2×100 mL) followed by ethyl ether (50 mL). The resulting solid was suspended in ethanol, collected by filtration and air dried to afford (1-benzyl-1H-imidazol-2-yl)(diphenyl)methyl acetate (1-3) as white crystals. $^1$H NMR (300 MHz, CDCl$_3$) δ 7.43 (m, 3H), 7.30 (m, 10H), 7.12 (d, 1H, J=1.2 Hz), 6.86 (m, 2H), 6.77 (d, 1H, J=1.2 Hz), 4.83 (s, 2H), 1.84 (s, 3H). LRMS m/z (M−OAc) 323.1 found, 323.2 required.

2-(diphenylmethyl)-1H-imidazole (1-4)

A slurry of (1-benzyl-1H-imidazol-2-yl)(diphenyl)methyl acetate (1-3, 13.1 g, 34.0 mmol, 1 equiv) and 10% palladium on carbon (6.03 g, 56.4 mmol, 1.66 equiv) in ethanol (250 mL) was stirred under hydrogen (balloon) for 24 h. The reaction mixture was filtered through a pad of celite and washed thoroughly with ethyl acetate. The combined filtrate was concentrated to dryness, and the residue was suspended in saturated aqueous sodium bicarbonate solution. The product was filtered, washed with water (2×100 mL) followed by a 1:1 mixture of ethyl ether and hexanes (2×50 mL) and air dried to yield 2-(diphenylmethyl)-1H-imidazole (1-4) as a white solid. $^1$H NMR (300 MHz, DMSO) δ 11.8 (br s, 1H), 7.29 (d, 6H, J=4.3 Hz), 7.21 (m, 4H), 7.03 (br s, 1H), 6.85 (br s, 1H), 5.51 (s, 2H), 1.84 (s, 3H). LRMS m/z (M+H) 235.0 found, 335.1 required.

2-(diphenylmethyl)-1-(1-phenylethyl)-1H-imidazole (1-5)

A mixture of 2-(diphenylmethyl)-1H-imidazole (1-4, 500 mg, 2.13 mmol, 1 equiv), 1-bromoethyl)benzene (0.874 mL, 6.40 mmol, 3.00 equiv) and potassium carbonate (1.48 g, 10.7 mmol, 5.01 equiv) in DMF (10 mL) was heated at 60° C. for 24 h. The resulting mixture was filtered and purified by reverse-phase HPLC (water/acetonitrile gradient w/0.01% TFA) to give 2-(diphenylmethyl)-1-(1-phenylethyl)-1H-imidazole (1-5) as a racemic mixture (white solid). $^1$H NMR (300 MHz, CDCl$_3$) δ 7.36-6.93 (m, 15H), 5.30 (s, 1H), 5.22 (q, 1H, J=7.2 Hz), 1.67 (d, 3H, J=7.0 Hz). LRMS m/z (M+H) 339.3 found, 339.2 required. Mineralocorticoid receptor binding affinity Ki value for 1-5 is 2857 nM.

The following compounds were prepared by simple modifications of the above procedures. Mineralocorticoid receptor binding affinity Ki values (nM) are shown after the compound name in parentheses.

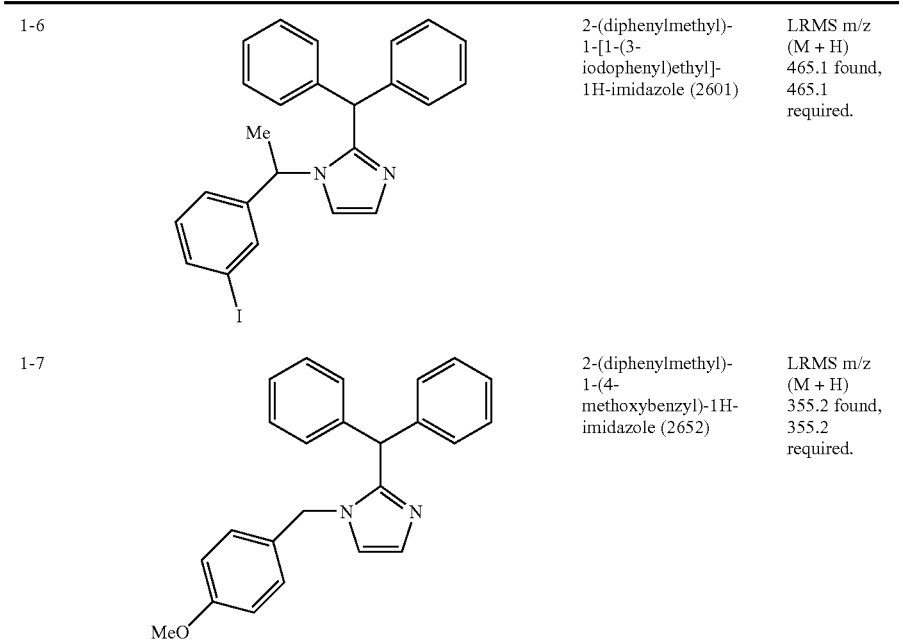

| | | |
|---|---|---|
| 1-6 | 2-(diphenylmethyl)-1-[1-(3-iodophenyl)ethyl]-1H-imidazole (2601) | LRMS m/z (M + H) 465.1 found, 465.1 required. |
| 1-7 | 2-(diphenylmethyl)-1-(4-methoxybenzyl)-1H-imidazole (2652) | LRMS m/z (M + H) 355.2 found, 355.2 required. |

| | | | |
|---|---|---|---|
| 1-8 | 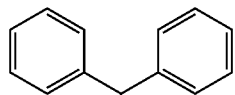 | 2-(diphenylmethyl)-1-[3-(trifluoromethyl)benzyl]-1H-imidazole (410.4) | LRMS m/z (M + H) 393.2 found, 393.2 required. |
| 1-9 | 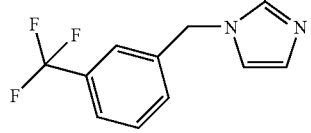 | 2-(diphenylmethyl)-1-{3-[(trifluoromethyl)thio]benzyl}-1H-imidazole | LRMS m/z (M + H) 425.2 found, 425.1 required. |
| 1-10 | 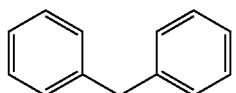 | 1-{1-[3,5-bis(trifluoromethyl)phenyl]ethyl}-2-(diphenylmethyl)-1H-imidazole (1086) | LRMS m/z (M + H) 475.3 found, 475.2 required. |
| 1-11 | 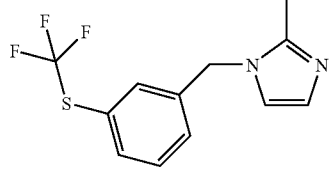 | 1-[3,5-bis(trifluoromethyl)benzyl]-2-(diphenylmethyl)-1H-imidazole (1351) | LRMS m/z (M + H) 461.3 found, 461.1 required. |
| 1-12 | 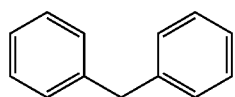 | 2-(diphenylmethyl)-1-(3-iodobenzyl)-1H-imidazole (287.2) | LRMS m/z (M + H) 451.0 found, 451.1 required. |

| | | | |
|---|---|---|---|
| 1-13 | 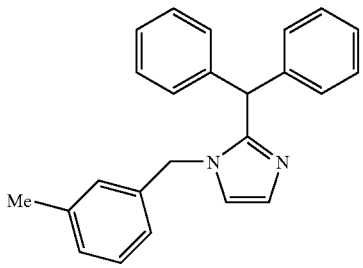 | 2-(diphenylmethyl)-1-(3-methylbenzyl)-1H-imidazole (134.4) | LRMS m/z (M + H) 339.4 found, 339.2 required. |
| 1-14 | 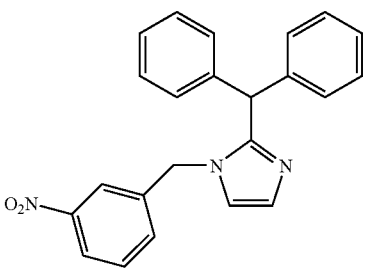 | 2-(diphenylmethyl)-1-(3-nitrobenzyl)-1H-imidazole (587.4) | LRMS m/z (M + H) 370.4 found, 370.1 required. |
| 1-15 | 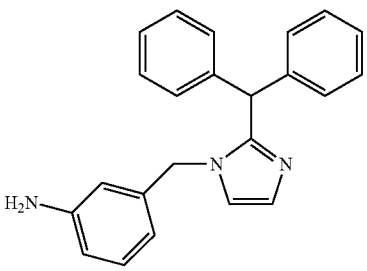 | 3-{[2-(diphenylmethyl)-1H-imidazol-1-yl]methyl}aniline (632.6) | LRMS m/z (M + H) 340.1 found, 340.2 required. |
| 1-16 | 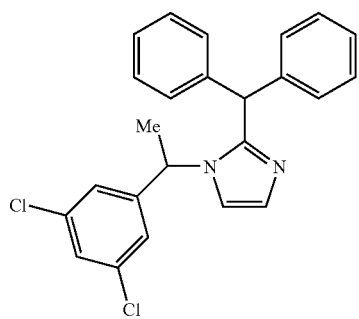 | 1-[1-(3,5-dichlorophenyl)ethyl]-2-(diphenylmethyl)-1H-imidazole (298.4) | LRMS m/z (M + H) 407.1 found, 407.1 required. |
| 1-17 | 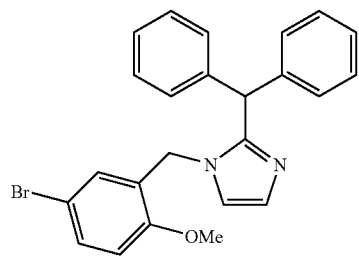 | 1-(5-bromo-2-methoxybenzyl)-2-(diphenylmethyl)-1H-imidazole (498.9) | LRMS m/z (M + H) 433.2 found, 433.1 required. |

-continued

| | | | |
|---|---|---|---|
| 1-18 | 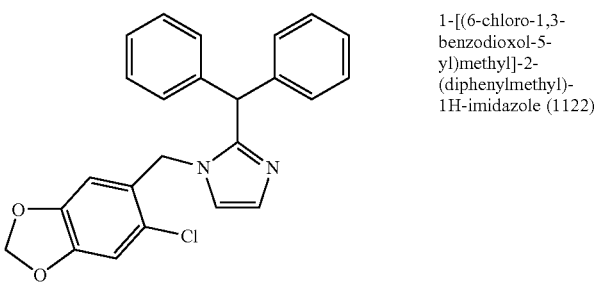 | 1-[(6-chloro-1,3-benzodioxol-5-yl)methyl]-2-(diphenylmethyl)-1H-imidazole (1122) | LRMS m/z (M + H) 403.2 found, 403.1 required. |
| 1-19 | 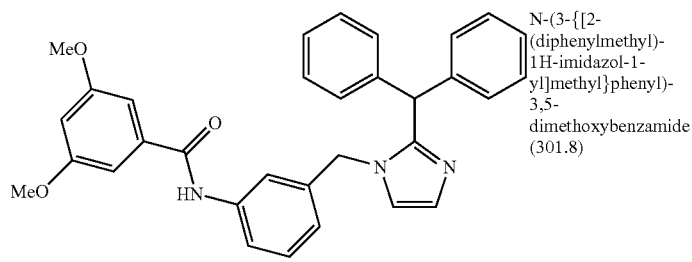 | N-(3-{[2-(diphenylmethyl)-1H-imidazol-1-yl]methyl}phenyl)-3,5-dimethoxybenzamide (301.8) | LRMS m/z (M + H) 504.2 found, 504.2 required. |
| 1-20 | 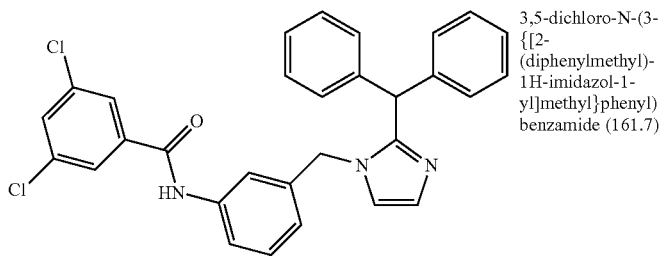 | 3,5-dichloro-N-(3-{[2-(diphenylmethyl)-1H-imidazol-1-yl]methyl}phenyl)benzamide (161.7) | LRMS m/z (M + H) 512.3 found, 512.1 required. |
| 1-21 | 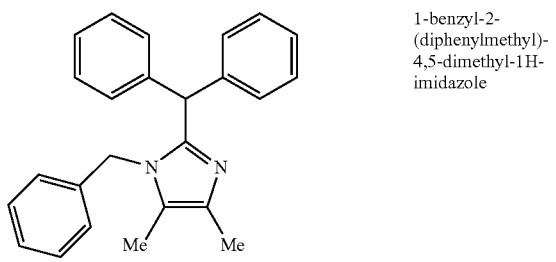 | 1-benzyl-2-(diphenylmethyl)-4,5-dimethyl-1H-imidazole | LRMS m/z (M + H) 353.4 found, 353.2 required. |

Scheme 2

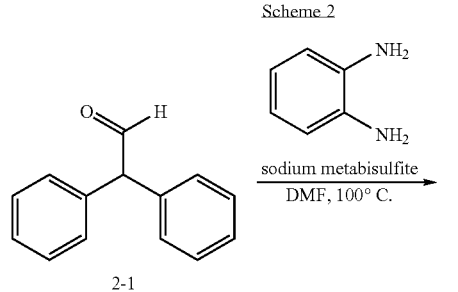 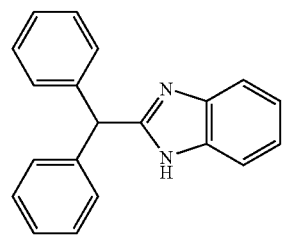

2-1　　　　　　　　　　　　　　　　　　　　2-2

2-(diphenylmethyl)-1H-benzimidazole (2-2)

A mixture of diphenylacetaldehyde (2-1, 1.64 mL, 9.25 mmol, 1 equiv), 1,2-diaminobenzene (0.787 mL, 9.25 mmol, 1.00 equiv) and sodium metabisulfite (2.11 g, 11.1 mmol, 1.20 equiv) in DMF (10 mL) was heated at 100° C. for 18 h. The reaction mixture was cooled to 23° C. and filtered. The filtrate was suspended with sonication in a 1:1 mixture of saturated aqueous sodium chloride solution and saturated aqueous sodium carbonate solution then extracted with ethyl acetate (6×150 mL). The combined organic layers were dried voer sodium sulfate and concentrated. The residue was suspended in ethyl ether (50 mL), filtered, washed with ethyl ether (2×50 mL) and air dried to give 2-(diphenylmethyl)-1H-benzimidazole (2-2) as a white solid. $^1$H NMR (300 MHz, DMSO) δ 12.3 (br s, 1H), 7.50 (m, 2H), 7.34 (m, 8H), 7.24 (m, 2H), 7.08 (m, 2H), 5.74 (s, 1H). LRMS m/z (M+H) 235.0 found, 335.1 required.

2-(diphenylmethyl)-1H-benzimidazole (2-2) was alkylated with the corresponding benzyl bromides according to the procedure described under Scheme 1 to provide compounds 2-3 and 2-4.

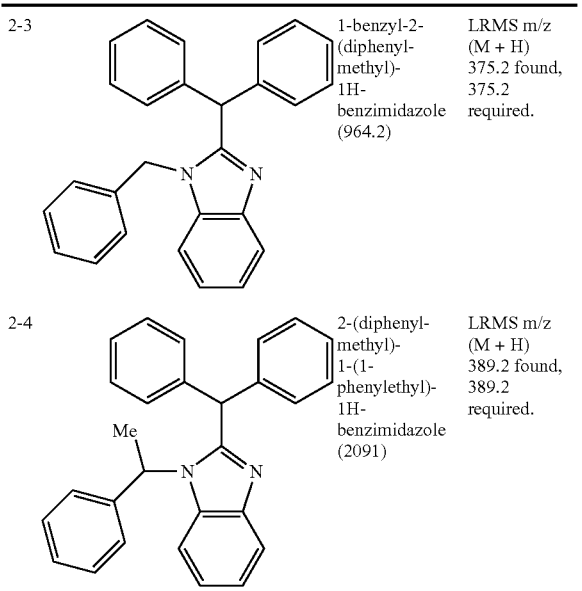

| | | | |
|---|---|---|---|
| 2-3 | | 1-benzyl-2-(diphenylmethyl)-1H-benzimidazole (964.2) | LRMS m/z (M + H) 375.2 found, 375.2 required. |
| 2-4 | | 2-(diphenylmethyl)-1-(1-phenylethyl)-1H-benzimidazole (2091) | LRMS m/z (M + H) 389.2 found, 389.2 required. |

Measurement of Mineralocorticoid Receptor Binding Affinity

The binding affinity of compounds for the mineralocorticoid receptor was determined by measuring their ability to prevent binding of radiolabeled aldosterone to recombinant rhesus mineralocorticoid receptor in a traditional filter binding assay protocol.

Rhesus mineralocorticoid receptor cDNA was cloned from a cDNA library using and used to prepare a recombinant baculovirus encoding the rhesus mineralocorticoid receptor coding sequence by standard molecular biological and cell biological methods. Insect cells grown in culture were infected with the recombinant baculovirus and this resulted in the expression of recombinant rhesus mineralocorticoid receptor in those cells. Cells were collected and lysed. The lysates were clarified by centrifugation and stored at −80 C until use in the radioligand binding assay.

The assays were carried out in 20 mM Hepes, 10 mM $Na_2MoO_4$, 10 mM 2-mercaptoethanol, 157 mM sucrose, and 3.7 mM CHAPS. [$^3$H]-Aldosterone (1 mCi/ml, 70-100 Ci/mmol) was purchased from Perkin Elmer (NET419). Test compounds were dissolved in DMSO and diluted in DMSO to 50 times the desired final concentrations for 3-fold serial dilution dose response curves. A working stock solution of [$^3$H]-aldosterone was prepared by dilution of the commercial stock to 0.083 μM in assay buffer. The insect cell lysate containing rhesus mineralocorticoid receptor was thawed and diluted to 0.7 mg protein/mL. Assay were started by combining 20 μL of test compound solution, 920 μL of diluted insect cell lysate, and 60 μL of [$^3$H]-aldosterone working solution in 2-mL 96-well polypropylene square well plates (USA Scientific) at 20° C. The mixture was incubated for 3 hr with continuous agitation on a platform shaker. The mixture was then filtered through 96-well GF/B filter plates (Packard) that had been previously treated with a solution of polyethylenimine (Sigma, P-3143). The filter plate was washed 3 times with 0.5 mL of 50 mM Tris-HCl, pH 7.4 and then dried overnight at 37° C. in a vacuum oven. The bottom of the plate was sealed and 40 μL of Microscint-20 (Packard, 6013621) was added to each well before counting radioactivity with a Topcount plate reader. Non-specific radioligand binding was determined by adding non-radiolabeled aldosterone (0.5 mM in DMSO) to the assay mixture to a final concentration of 10 μM in place of test compound. $IC_{50}$ and Ki values were determined using a four parameter logistic fit using a customized assay data analyzer software package.

Examples were tested in the ligand binding assay and demonstrated $IC_{50}$s less than 10,000 nM.

What is claimed is:
1. A compound of formula I,

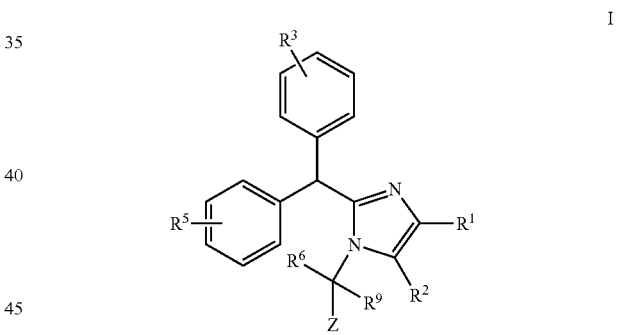

and pharmaceutically acceptable salts thereof, or an optical isomer thereof, wherein Z is selected from the group consisting of
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S, and
   c) an 8-, 9- or 10-membered unsaturated bicyclic ring with 1, 2, 3, or 4 heteroatom ring atoms selected from the group consisting of N, O or S, and
3) a 4-6 membered saturated heterocyclic ring with 1, 2 or 3 heteroatom ring atoms selected from the group consisting of N, O and S, wherein the point of attachment to the heterocyclic ring is a carbon atom, said aryl, heteroaryl, saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo, said heteroaryl ring $R^4$ substitutions being on one or more heteroaryl ring carbon atoms;

$R^1$ and $R^2$ are selected from the group consisting of hydrogen and $C_1$-$C_6$ alkyl, or $R^1$ and $R^2$, together with the carbon atoms to which they are attached, form a benzimidazole ring substituted at the 1- and 2-positions;

$R^3$ and $R^5$ are selected from the group consisting of hydrogen, halogen, $C_1$-$C_6$ alkyl, $C_1$-$C_6$ alkoxy, OH, and CN;

$R^4$ is selected from the group consisting of $C_1$-$C_6$ alkyl, $C_1$-$C_6$ alkoxy, halogen, $NO_2$, $NH_2$, $CF_3$, $SCF_3$, NHC(O)$R^7$, OH, CN, $NR^aR^b$, $CONR^aR^b$, $CO2Ra$, $C(O)0$-$2R^a$, $SO2NR^aR^b$, where $R^a$ and $R^b$ are independently selected from the group consisting of hydrogen and $C_1$-$C_6$ alkyl, or $R^a$ and $R^b$, together with the N atom to which they are attached, form a 3-8-membered ring containing the N atom and 1-3 heteroatoms selected from the group consisting of N, O and S;

$R^6$ and $R^9$ are independently selected from the group consisting of hydrogen and $C_1$-$C_6$ alkyl;

$R^7$ is selected from the group consisting of
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S, and
   c) an 8-, 9- or 10-membered unsaturated bicyclic ring with 1, 2, 3, or 4 heteroatom ring atoms selected from the group consisting of N, O or S, and
3) $C_1$-$C_6$ alkyl, wherein said aryl ring, heteroaryl ring, and $C_1$-$C_6$ alkyl is unsubstituted, mono-substituted with $R^8$, disubstituted with groups independently selected from $R^8$, trisubstituted with groups independently selected from $R^8$, or tetrasubstituted with groups independently selected from $R^8$, and wherein any stable S or N heteroaryl ring atom is unsubstituted or substituted with oxo, said heteroaryl ring $R^8$, substitutions being on one or more heteroaryl ring carbon atoms; and $R^8$ is independently selected from the group consisting of $C_1$-$C_6$ alkyl, $C_1$-$C_6$ alkoxy, OH, CN and halogen.

2. A compound of claim 1, or a pharmaceutically acceptable salt thereof, wherein Z is selected from the group consisting of an aryl ring and 9-membered unsaturated heteroaryl bicyclic ring with 1 or 2 heteroatom ring atoms, wherein the heteroatom is O, wherein said aryl or heteroaryl bicyclic ring is unsubstituted, mono-substituted with $R^4$, disubstituted with groups independently selected from $R^4$, trisubstituted with groups independently selected from $R^4$, or tetrasubstituted with groups independently selected from $R^4$, said heteroaryl ring $R^4$ substitutions being on one or more heteroaryl ring carbon atoms.

3. A compound of claim 2, or a pharmaceutically acceptable salt thereof, wherein $R^4$ is selected from the group consisting of $CH_3$, $OCH_3$, halogen, $NO_2$, $NH_2$, $CF_3$, $SCF_3$, Cl, Br, I, and NHC(O)$R^7$.

4. A compound of claim 3, or a pharmaceutically acceptable salt thereof, wherein $R^7$ is aryl, either unsubstituted, mono-substituted with $CH_3$ or Cl, or independently di-substituted with a substituent selected from the group consisting of $CH_3$ and Cl.

5. A compound of claim 4, or a pharmaceutically acceptable salt thereof, wherein Z is selected from the group consisting of

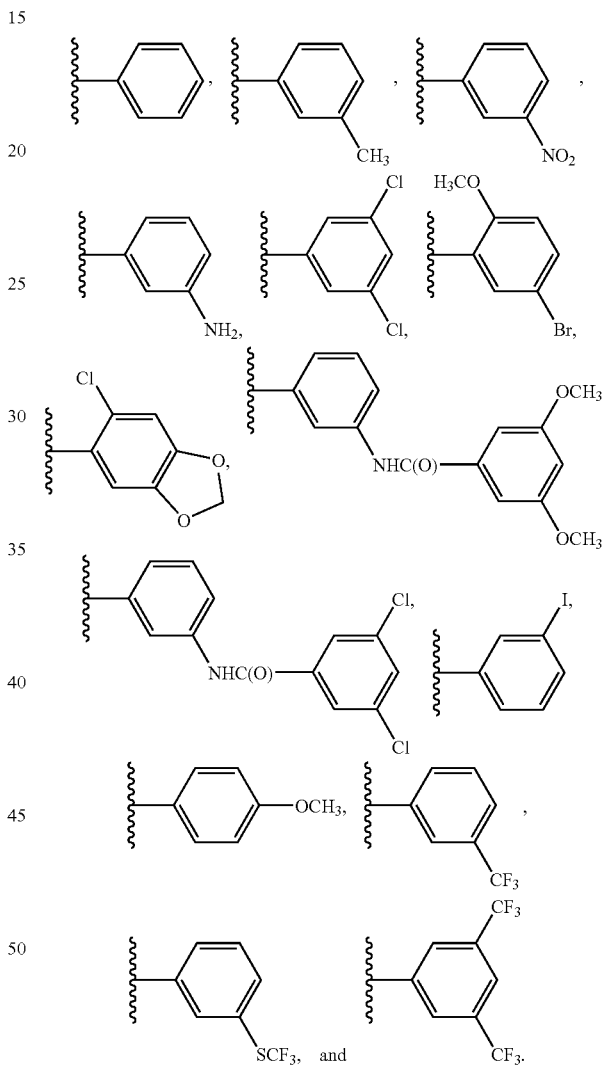

6. A compound of claim 1, or a pharmaceutically acceptable salt thereof, wherein $R^1$ and $R^2$ are selected from the group consisting of hydrogen and $CH_3$, or $R^1$ and $R^2$, together with the carbon atoms to which they are attached, form a benzimidazole ring substituted at the 1- and 2-positions.

7. A compound of claim 1, or a pharmaceutically acceptable salt thereof, wherein $R^3$ and $R^5$ are hydrogen.

8. A compound of claim 1, or a pharmaceutically acceptable salt thereof, wherein $R^6$ is selected from the group consisting of hydrogen and $CH_3$.

9. A compound of claim 1, or a pharmaceutically acceptable salt thereof, selected from the group consisting of:
- 2-(diphenylmethyl)-1-(1-phenylethyl)-1H-imidazole,
- 2-(diphenylmethyl)-1-[1-(3-iodophenyl)ethyl]-1H-imidazole,
- 2-(diphenylmethyl)-1-(4-methoxybenzyl)-1H-imidazole,
- 2-(diphenylmethyl)-1-[3-(trifluoromethyl)benzyl]-1H-imidazole,
- 2-(diphenylmethyl)-1-{3-[(trifluoromethyl)thio]benzyl}-1H-imidazole,
- 1-{1-[3,5-bis(trifluoromethyl)phenyl]ethyl}-2-(diphenylmethyl)-1H-imidazole,
- 1-[3,5-bis(trifluoromethyl)benzyl]-2-(diphenylmethyl)-1H-imidazole,
- 2-(diphenylmethyl)-1-(3-iodobenzyl)-1H-imidazole,
- 2-(diphenylmethyl)-1-(3-methylbenzyl)-1H-imidazole,
- 2-(diphenylmethyl)-1-(3-nitrobenzyl)-1H-imidazole,
- 3-{[2-(diphenylmethyl)-1H-imidazol-1-yl]methyl}aniline, 1-[1-(3,5-dichlorophenyl)ethyl]-2-(diphenylmethyl)-1H-imidazole,
- 1-(5-bromo-2-methoxybenzyl)-2-(diphenylmethyl)-1H-imidazole,
- 1-[(6-chloro-1,3-benzodioxol-5-yl)methyl]-2-(diphenylmethyl)-1H-imidazole,
- N-(3-{[2-(diphenylmethyl)-1H-imidazol-1-yl]methyl}phenyl)-3,5-dimethoxybenzamide,
- 3,5-dichloro-N-(3-{[2-(diphenylmethyl)-1H-imidazol-1-yl]methyl}phenyl)benzamide,
- 1-benzyl-2-(diphenylmethyl)-4,5-dimethyl-1H-imidazole,
- 2-(diphenylmethyl)-1H-benzimidazole,
- 1-benzyl-2-(diphenylmethyl)-1H-benzimidazole, and
- 2-(diphenylmethyl)-1-(1-phenylethyl)-1H-benzimidazole.

10. A pharmaceutical composition comprising an effective amount of a compound according to claim 1, or a pharmaceutically acceptable salt thereof, and a pharmaceutically acceptable carrier.

11. A method for the treatment of hypertension or heart failure, comprising administering a therapeutically effective amount of a compound according to claim 1, or a pharmaceutically acceptable salt thereof, to a subject in need thereof.

* * * * *